United States Patent [19]

Finotto

[11] Patent Number: 4,642,367

[45] Date of Patent: Feb. 10, 1987

[54] PROCESS FOR THE PREPARATION OF ALFA-L-ASPARTYL-L-PHENYL-ALANINE ALKYL ESTERS

[75] Inventor: Martino Finotto, Treviglio, Italy

[73] Assignee: Farchemia S.p.A., Treviglio, Italy

[21] Appl. No.: 755,063

[22] Filed: Jul. 15, 1985

[30] Foreign Application Priority Data

Aug. 1, 1984 [IT] Italy ............................. 22177 A/84
Dec. 4, 1984 [IT] Italy ............................. 23876 A/84
Apr. 9, 1985 [IT] Italy ............................. 47942 A/85

[51] Int. Cl.⁴ ...................... C07C 101/32; C07K 1/06
[52] U.S. Cl. .................................. 560/40; 260/998.21; 530/801
[58] Field of Search ................. 260/998.21; 560/40; 530/801

[56] References Cited

U.S. PATENT DOCUMENTS 3,814,747 6/1974 Lapidus et al. ................ 260/998.21

Primary Examiner—Delbert R. Phillips
Attorney, Agent, or Firm—Bucknam and Archer

[57] ABSTRACT

A new process for preparing alfa-L-aspartyl-L-phenylalanine alkyl esters of formula I wherein R represents an alkyl group having from 1 to 5 carbon atoms, starting from the corresponding alfa-haloacyl-alfa-L-aspartyl-L-phenylalanine alkyl esters.

8 Claims, No Drawings

PROCESS FOR THE PREPARATION OF ALFA-L-ASPARTYL-L-PHENYL-ALANINE ALKYL ESTERS

The present invention relates to a new process for preparing alfa-L-aspartyl-L-phenylalanine alkyl esters of formula I

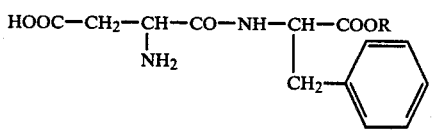

wherein R represents an alkyl group having from 1 to 5 carbon atoms, starting from the corresponding alfa-halo-acyl-alfa-L-aspartyl-L-phenylalanine alkyl esters (II) according to the following reaction scheme:

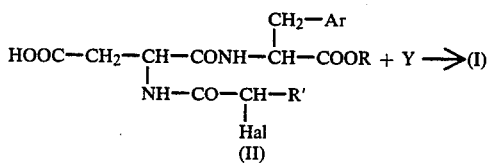

wherein:
R is as above defined;
Ar is the phenyl group;
R' represents hydrogen or a $C_1$-$C_4$, linear or branched alkyl group;
Hal represents chlorine, bromine or iodine;
Y is a compound selected from the group consisting of thiourea, cyanic acid salts, thiocyanic acid salts, dithiocarbamic acid salts, guanidine, 1,2-ethanedithiol, cysteamine, ethanolamine, ethylenediamine, 1,2-diaminobenzene, 1,2-dimercaptobenzene, pyrocatechol, o-aminophenol.

In a preferred embodiment of the process according to the invention, R' represents hydrogen or a methyl group; Hal is chlorine or bromine; Y is thiourea.

In a particularly preferred aspect, the present invention provides a process for preparing alfa-L-aspartyl-L-phenylalanine methyl ester (I, wherein R=CH$_3$) or aspartame.

Aspartame is a well known sweetening agent widely used as dietetic sweetening agent, due to its taste very similar to that of saccharose.

Dipeptides of formula (I) are known to be prepared starting from L-aspartic acid derivatives. According to a known method, the process is carried out starting from L-aspartic acid in which both the —NH$_2$ and β- and alfa-carboxylic groups have been protected by means, for example, of benzyloxycarbonyl or formyl or 4-nitrophenylester groups: by reaction with a L-phenylalanine ester the 4-nitrophenyl group is removed and the protected dipeptide is obtained, from which the other protecting groups can be removed by such conventional techniques as hydrogenolysis or hydrolysis.

However, selective esterification of the β-carboxylic group of L-aspartic acid is difficult to perform and, moreover, it takes place in low yields; on the other hand to produce aspartame it is necessary that condensation should occur only on the alfa-carboxylic group.

According to another known method a N-protected L-aspartic anhydride is employed as the starting material; however, the condensation of said anhydride with aminoacids or aminoacid esters (namely, L-phenylalanine methyl ester) followed by removal of the protecting group always gives final products which contain small but not negligeable quantities of alfa-L-aspartyl-L-phenylalanine and of (2-benzyl-3,6-dioxo-piperazin-5-yl)acetic acid (the so called "diketopiperazine").

This is the case, too, of the deformylation of N-formyl-alfa-L-aspartyl-L-phenylalanine esters with hydrazine or acylhydrazines, as described in more recent patent applications.

The drawbacks of the methods according to the prior art are overcome by the process of the present invention, which allows to obtain easily and in high yields alfa-L-aspartyl-L-phenylalanine alkyl esters which are characterized by a very good purity.

According to the invention, the N-alfa-haloacyl esters (I) are prepared by reaction of the corresponding N-alfa-haloacyl-L-aspartic acid anhydrides (III) with L-phenylalanine alkyl esters (IV)

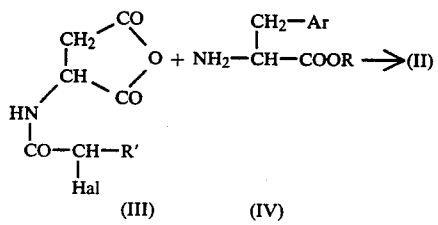

wherein R, R', Ar and Hal are as above defined. In their turn, the anhydrides (III) are obtained from L-aspartic acid and alfa-haloacid chlorides (or bromides) R'—CH-(Hal)—COCl (or R'—CH(Hal)—COBr), wherein R' and Hal are as above defined, according to conventional N-acylation methods, followed by treatment with a dehydrating agent, preferably acetic acid anhydride. Alternatively, the compounds (III) are directly prepared by reacting L-aspartic acid with alfa-haloacid anhydrides of the formula (V)

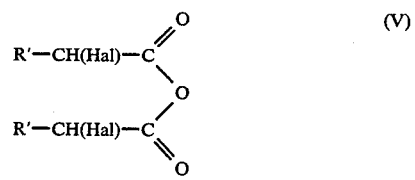

wherein R' and Hal are as above defined. This reaction, which represents a preferred embodiment in the preparation of the anhydrides (III), is preferably carried out in inert solvents, such as aromatic hydrocarbons (benzene, toluene) or haloalkanes (CCl$_4$, CHCl$_3$, tetrachloroetane), at temperatures ranging from 0° C. to 100° C., preferably from 30° C. to 60° C. The alfa-haloacid anhydrides (V) are preferably used in a small excess; generally 2.1–2.3 moles of (V) pro mole of L-aspartic acid are used. The separation of the N-alfa-haloacyl-L-aspartic acid anhydride (III) from the alfa-haloacid R'—CH(Hal)—COOH formed as a by-product is easily achieved, for instance by crystallisation from ethyl acetate.

The following acylation of the L-phenylalanine alkyl esters (IV) with (III) is preferably carried out in inert solvents (preferably lower esters, such as ethyl acetate, or aromatic hydrocarbons, or lower ketones, or chloroalkanes), at temperatures ranging from −20° C. to +50° C., preferably from 0° C. to +20° C. A particularly pure product, in particularly high yields, is obtained when a lower alkanoic acid, preferably acetic acid, is added to the reaction mixture.

Alternatively, the alfa-haloacyl-alfa-L-aspartyl-L-phenylalanine alkyl esters (II) may be prepared, according to the invention, starting from L-asparagine derivatives, i.e. from derivatives of a commercially available, natural product having the β-carboxylic group already "blocked".

According to the invention, a N-alfa-haloacyl-L-asparagine (VI) is condensed with a L-phenylalanine alkyl ester (IV) to give a dipeptide derivative (VII) the amido group of which is selectively transformed into a carboxylic group, as shown in the following reaction scheme:

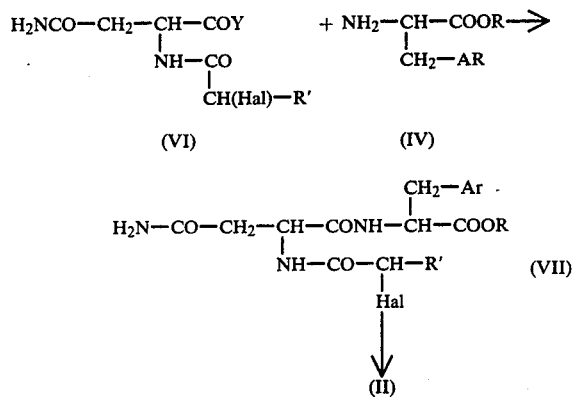

wherein R, R', Ar and Hal are as above defined, whereas Y represents OH or an activating atom or group; more particularly, Y represents hydroxy, alcoxycarbonyloxy, o-nitrophenoxy or an O-N-succinimido group.

Both the alfa-haloacyl group and Y can be inserted in the L-asparagine molecule easily and in high yields, the resulting derivatives being generally crystalline compounds which can be easily isolated in a pure form.

The condensation of the L-asparagine derivative (VI) with a L-phenylalanine alkyl ester (IV) is conveniently carried out under different conditions, depending on the nature of the Y group.

When Y=OH, the condensation with compound (IV) may be advantageously carried out with dicyclohexylcarbodiimide in the presence of N-hydroxy-succinimide, in reaction mediums such as dimethylformamide. Alternatively, the same condensation may also be effected using pivaloyl chloride in the presence of tertiary bases, such as pyridine and N-ethylpiperidine, in solvents such as methylene chloride or dimethylformamide. On the other hand, when Y=o-nitrophenyl, the condensation may be carried out by simple treatment with compound (IV) at room temperature, for example in acetonitrile/pyridine as the solvent.

The reaction mixture is concentrated under vacuum, then diluted with water and the resulting dipeptide (VII) is recovered by filtration. The dipeptide may be subsequently washed with a sodium carbonate solution, with diluted hydrochloric acid and with water and it may be used as such for the next step or it can be optionally recrystallized with, for example, methanol.

The conversion of asparaginyl-dipeptide (VII) in aspartyl-dipeptide (II) is carried out with nitrosonium salts, such as nitrosyl tetrafluoborate or sulfate, or with inorganic or organic nitrites in the presence of mineral acids.

The reaction is advantageously carried out by reacting compound (VII) with nitrosylsulfuric acid in glacial acetic acid, or in acetonitrile or dimethylformamide, at room temperature for about 4 hours, under strong stirring. Compound (II) may be precipitated by addition of ice-water and recovered by filtration.

The reaction of the alfa-haloacyl-alfa-L-aspartyl-L-phenylalanine alkyl esters (II) with Y is carried out at temperatures ranging from 20° C. to 80° C., advantageously in protic solvents, at pH-values between 0 and 8. The reaction time depends on the specific compound Y used to remove the alfa-haloacyl group, and on the reaction temperature. As above mentioned, said removal is achieved in a particularly easy way by reaction of (II) with thiourea and decomposition of the resulting isothiouronium salt, according to the scheme:

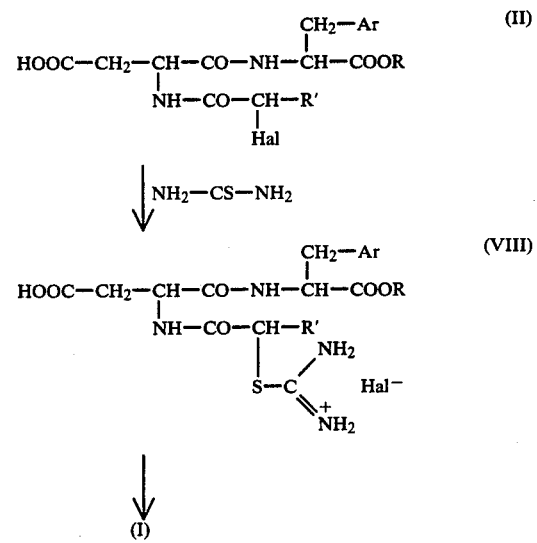

wherein R, R', Ar and Hal have the above defined meanings.

The recovery of the isothiouronium salt (VIII) is not necessary since the preparation of the final esters (I) from the haloacyl derivatives (II), turns out to be very easy without isolating said salts, by operating preferably in protic solvents selected in the group consisting of lower alcohols, water and their mixtures, at pH values ranging from 0 to 8 and at temperatures ranging from 20° C. to 80° C. At the end of the reaction, the pseudo-thiohydantoin formed as a by-product is filtered out, and the final esters (I) are isolated in a per se known manner.

The following non limitative examples are reported for sake of illustration of the process according to the present invention.

EXAMPLE 1

(a) N-Chloroacetyl-L-aspartic acid anhydride (III, wherein R'=H, Hal=Cl)

200 Grams (1.05 moles) of monochloroacetic acid anhydride and 67 grams (0.5 moles) of L-aspartic acid are heated to 40° C. for 8 hours. The raw product is washed twice with 150 ml of toluene, then heated to 50° C. with 100 ml of ethyl acetate. By cooling to 0° C. 69 grams (72%) of a product melting at 157°–159° C. are obtained.

Analysis: for $C_6H_6ClNO_4$ (MW=191.5) calcd. %: C=37.59; H=3.13; N=7.31; Cl=18.53; found %: C=37.72; H=3.17; N=7.19; Cl=18.38.

NMR-spectrum (in hexadeuterodimethylsulfoxide, v. TMS; signals are given as $\delta$): 2.6–4.5, multiplet (AB-portion of an ABX-system), 2H: $CH_2$—CH; 4.2, singlet, 2H: $CH_2$—Cl; 4.8, multiplet, 1H: $\overline{CH}$—$CH_2$; 9.15, doublet, 1H: NH.

(b) N-Chloroacetyl-alfa-L-aspartyl-L-phenylalanine methyl ester (II, wherein R=$CH_3$, R'=H, Hal=Cl)

50 grams (0.26 moles) of N-chloroacetyl-L-aspartic acid anhydride are added, in about 30 minutes, to the stirred solution of 46.5 grams (0.26 moles) of L-phenylalanine methyl ester in 300 ml of acetonitrile, at a temperature of about 0° C. Stirring is continued for 1 hour at the same temperature, then the mixture is heated to 40° C. for 2 hours. After standing at 10° C. for 15 hours the crystalline product is filtered and washed with 150 ml of cool $CH_3CN$: 81 grams (84%) of N-chloroacetyl-aspartame are obtained, m.p. 135°–139° C. (ca. 60% of alfa-isomer and 40% of beta-isomer).

Analysis: for $C_{16}H_{19}ClN_2O_{16}$ (MW=370.5) calcd. %: C=51.82; H=5.12; N=7.56; found %: C=51.49; H=5.17; N=7.49.

(c) alfa-L-Aspartyl-L-phenylalanine methyl ester (aspartame) (I, wherein R=$CH_3$)

A solution of 40 grams (0.107 moles) of N-chloroacetyl-aspartame and 8.5 grams (0.111 moles) of thiourea in 100 ml of methanol is refluxed for 6 hours, then cooled to +5° C., and the pseudothiohydantoin is filtered by suction. The filtrate is evaporated to dryness; the residue is heated to 30° C. with a mixture of 13 ml of 30% HCl and 70 ml of water. The solution is cooled to 10° C. in about 6 hours, the crystalline product is filtered by suction and washed with cooled water (20 ml). A pure aspartame hydrochloride is obtained in an overall yield of 34%.

EXAMPLE 2 alfa-L-Aspartyl-L-phenylalanine methyl ester (aspartame) (I, wherein R=$CH_3$)

150 Grams of N-chloroacetyl-L-aspartic acid anhydride are quickly added, at −5° C., to the solution of 140 grams of methyl L-phenylalaninate in 400 ml of dichloroethane plus 200 ml of acetic acid. The mixture is stirred for 1 hour at −5° C.; the temperature is then raised, in 2 hours, to 15° C., then, in 30 minutes, to 40° C. The dichloroethane is evaporated under vacuum; 500 ml of methanol and 60 grams of thiourea are added and the mixture is refluxed for 3 hours. After cooling to 20° C., 200 ml of methanol, containing 11% (by weight) of HCl, are added, the solution is cooled to 0° C. for 1 hour, filtered and evaporated to dryness in vacuo. The residue is crystallized from 600 ml of water containing 70 g of NaCl: a very pure aspartame hydrochloride is obtained, in a 48% yield.

EXAMPLE 3

(a) N-Chloroacetyl-L-aspartic acid anhydride (III, wherein R'=H, Hal=Cl)

To the mixture of 210 grams (1.23 moles) of monochloroacetic acid anhydride and 100 ml of $CHCl_3$, 67 grams (0.5 moles) of L-aspartic acid are added. After stirring for 6 hours at 40°–45° C., 400 ml of $CHCl_3$ are added and the warm suspension is filtered by suction. The product is treated with 200 ml of $CHCl_3$, in order to remove the chloroacetic acid as much as possible, filtered by suction, washed on the filter with some $CHCl_3$ and dried under vacuum at 40° C.: 88 grams of a very pure product are obtained, m.p. 157°–159° C.

Potentiometric titration (morpholine): 98%.
Yield: 91.9%.

From the mother liquors, monochloroacetic acid can easily be recovered.

(b) N-Chloroacetyl-alfa-L-aspartyl-L-phenylalanine methyl ester (II, wherein R=$CH_3$, R'=H, Hal=Cl)

To the mixture of 60 grams (0.32 moles) of N-chloroacetyl-aspartic acid anhydride, 100 ml of ethyl acetate and 80 ml of acetic acid, stirred at 5°–10° C., the solution of 58 grams (0.32 moles) of L-phenylalanine methyl ester in 200 ml of ethyl acetate is added, in about 1 hour. The mixture is stirred for 4 hours at 5°–10° C., then for 2 hours at room temperature. The precipitate is pump filtered: 113 grams of product are obtained, m.p. 147°–149° C. (96% yield); potentiometric assay (NaOH 0.1N) 98%; by HPLC, 80% of alfa-isomer and 20% of beta-isomer are identified.

(c) alfa-L-Aspartyl-L-phenylalanine methyl ester (aspartame) (I, wherein R=$CH_3$)

A mixture of 100 grams (0.27 moles) of methyl ester of N-chloroacetyl-alfa-L-aspartyl-L-phenylalanine (80% alfa—20% beta), 21 grams (0.21 moles) of thiourea and 300 ml of methanol is refluxed for 5 hours. After cooling to +5° C., the precipitated thiohydantoin is filtered by suction. The filtrate is evaporated in vacuo to a small volume, then treated with 60 ml of acetic acid, 140 ml of water and 30 ml of 30% HCl. The residue methanol is evaporated in vacuo and the solution is seeded, at 40° C., with aspartame hydrochloride; then it is slowly cooled to +5° C. and left to stand overnight at this temperature. The precipitate is recovered by suction and washed with 30 ml of ice-cooled water. From this hydrochloride, 40 grams of a very pure aspartame are obtained with conventional methods. The yield is 50% on the raw product (62.5% on the alfa isomer). M.p. 240°–248° C.; $[\alpha]_D^{20}$=15.5 (4% in formic acid); potentiometric assay: (a) with tetrabutylammonium hydroxyde=99.5%; (b) with $HClO_4$=99.5% (dry product); "diketopiperazine" <0.3%; pseudothiohydantoin <0.3%; "beta"-aspartame: absent.

From the mother liquors, by severe hydrolysis, 18.5 g of L-phenylalanine are recovered.

EXAMPLE 4

(a) alfa-Bromopropionyl-L-asparaginyl-L-phenylalanine methyl ester (VII, wherein R=R'=$CH_3$, Hal=Br)

26.7 Grams (0.1 moles) of finely pulverized alfa-bromopropionyl-L-asparagine (obtained from L-asparagine and alfa-bromopropionyl chloride according to Schotten-Baumann) were dissolved in 100 ml of dimethylformamide, by addition of 8 ml of pyridine and 28 ml of N-ethyl-piperidine. The solution, under strong stirring, was rapidly cooled to −30° C.; the resulting suspension was treated with 12 g of pivaloyl chloride dissolved in 20 ml of dimethylformamide. The clear solution obtained was treated, after about 30 minutes, with 22 g of L-phenylalanine methyl ester hydrochloride. The mixture was kept at −30° C. for 30 minutes and then allowed to raise spontaneously to room temperature in about 2 hours. The solution concentrated under vacuum was poured in 1 liter of water and the suspension kept under stirring for some hours. The precipitated product was filtered, washed with water and dried under vacuum, obtaining 30 g, 70% yield.

After acid hydrolysis of the product in closed vial for 22 hours in HCl 6M at 110°, the analysis in aminoacids gave a phenylalanine:aspartic acid ratio=1:0.97 with a 99.2% yield.

(b) alfa-L-Aspartyl-L-phenylalanine methyl ester (I, wherein R=CH₃)

21.4 Grams (0.05 moles) of alfa-bromopropionyl-L-asparaginyl-L-phenylalanine methyl ester, dissolved in 150 ml of dimethylformamide, were treated with 15 ml of 6M HCl solution in dioxane and then with 10.5 g of n-butylnitrite, added in about 20 minutes. After 6-8 hours at room temperature under constant stirring, the mixture was concentrated to dryness and the residue taken up with 100 ml of absolute methanol. 3.8 Grams (0.05 moles) of thiourea were added to the resulting mixture, and it was then refluxed for 20 minutes. The methanolic suspension of the isothiouronium bromide so obtained (VIII, wherein R=R'=CH₃ and Hal=bromine) was concentrated to dryness and the residue taken up with 100 ml of water; the pH of the solution was brought to 7-8 with NaHCO₃, the mixture was then heated to 40° for 2 hours. After cooling at room temperature, the mixture was acidified to pH 4.5 with 2M HCl and then concentrated under vacuum. 11.47 Grams of aspartame, substantially identical to that obtained in the previous examples, were obtained.

EXAMPLE 5

(a) N-Chloroacetyl-alfa-L-aspartyl-L-phenylalanine ethyl ester (II, wherein R=C₂H₅, R'=H, Hal=Cl)

5 Grams of N-chloroacetyl-L-aspartic acid anhydride were added, in 10 minutes, under stirring to 4.8 grams of ethyl L-phenylalaninate in 50 ml of CH₃CN, at about 0° C. The mixture was stirred for 30 minutes at 0° C., then for 2 hours at 40° C., and filtered by suction. After washing with 20 ml of ice-cooled CH₃CN, 7.5 g of the title product were obtained, m.p. 118°-120° C.

(b) alfa-L-Aspartyl-L-phenylalanine ethyl ester (I, wherein R=C₂H₅)

To the solution of the product obtained in (a) in 30 ml of methanol, 1.7 g of thiourea were added. After refluxing for 5 hours the mixture was cooled to 0° C. and the pseudothiohydantoin was removed by pump filtration. The mother liquor was evaporated to dryness, the residue was treated at 30° C. with 2 ml of 30% HCl in 10 ml of water. After cooling to +5° C., the crystalline product was filtered by suction. The title product was obtained (as hydrochloride) in a 38% yield.

Analysis: for C₁₅H₂₁ClN₂O₅ (MW=344.5) calcd. % C=52.25; H=6.09; N=8.13; found % C=52.03; H=6.19; N=8.03.

In the same manner, the isobutyl ester of alfa-L-aspartyl-L-phenylalanine was obtained.

EXAMPLE 6

Operating as described in Example 2, but using sodium thiocyanate instead of thiourea, aspartame was obtained in an overall 22% yield.

EXAMPLE 7

The procedure of Example 1 was repeated using—instead of thiourea—equimolecular quantities of the following compounds: potassium cyanate; sodium dithiocarbamate; guanidine; cysteamine; ethylenediamine; pyrocatechol.

Aspartame was obtained, with yields ranging from 10 to 15%.

EXAMPLE 8

The procedure of Example 2 was repeated, with the exception that the alfa-haloacyl group was the alfa-bromo-hexanoyl group (R'=n-butyl). Aspartame of a very good purity was obtained; 43% yield.

I claim:

1. Process for the preparation of alkyl esters of alfa-L-aspartyl-L-phenylalanine of the formula (I)

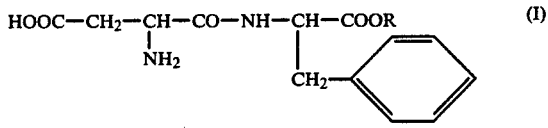

wherein R is a C₁-C₅ alkyl group, characterized in that alfa-haloacyl-alfa-L-aspartyl-L-phenylalanine alkyl esters of the formula (II)

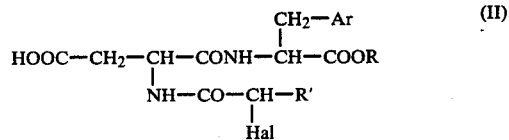

wherein:
R is as above defined;
Ar is the phenyl group;
R' represents hydrogen or a C₁-C₄ linear or branched alkyl group;
Hal represents chlorine, bromine or iodine,
are reacted with a compound selected from the group consisting of thiourea, cyanic acid salts, thiocyanic acid salts, dithiocarbamic acid salts, guanidine, 1,2-ethanedithiol, cysteamine, ethanolamine, ethylenediamine, 1,2-diaminobenzene, 1,2-dimercaptobenzene, pyrocatechol, o-aminophenol.

2. Process as claimed in claim 1, characterized in that the reaction is carried out in protic solvents.

3. Process as claimed in claim 2, characterized in that the solvent is selected in the group consisting of lower alcohols, water and mixtures thereof.

4. Process as claimed in claim 1 characterized in that the reaction is carried out at pH values ranging from 0 to 8.

5. Process as claimed in claim 1 characterized in that the reaction temperature ranges from 20° C. to 80° C.

6. Process as claimed in claim 1 characterized in that the alfa-haloacyl-alfa-L-aspartyl-L-phenylalanine alkyl esters (II) are reacted with thiourea.

7. As new products, alfa-haloacyl-alfa-L-aspartyl-L-phenylalanine alkyl esters of the formula (II)

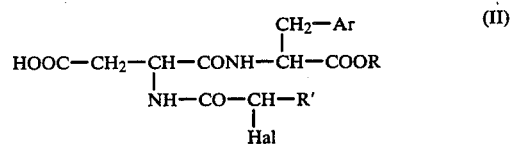

wherein R, R', Ar and Hal are as above defined.

8. New products according to claim 7, characterized in that R is a methyl group.

* * * * *